United States Patent
Gabel et al.

(10) Patent No.: US 9,489,251 B2
(45) Date of Patent: Nov. 8, 2016

(54) SUPERVISING AND RECOVERING SOFTWARE COMPONENTS ASSOCIATED WITH MEDICAL DIAGNOSTICS INSTRUMENTS

(75) Inventors: Shlomo Gabel, Shoam (IL); Eliran Tamir, Shoam (IL); Zviya Tamir, legal representative, Natniya (IL); Moshe Tamir, legal representative, Natniya (IL)

(73) Assignee: BIO-RAD LABORATORIES, INC., Hercules, CA (US)

( * ) Notice: Subject to any disclaimer, the term of this patent is extended or adjusted under 35 U.S.C. 154(b) by 374 days.

(21) Appl. No.: 13/311,971

(22) Filed: Dec. 6, 2011

(65) Prior Publication Data
US 2013/0145204 A1 Jun. 6, 2013

(51) Int. Cl.
G06F 11/00 (2006.01)
G06F 11/07 (2006.01)
G06F 19/00 (2011.01)

(52) U.S. Cl.
CPC ....... G06F 11/0793 (2013.01); G06F 11/0736 (2013.01); G06F 19/3412 (2013.01)

(58) Field of Classification Search
CPC .......... A61B 15/0002; A61B 15/0005; A61B 15/0008; G06Q 20/10; G06Q 30/06; G06F 19/3406; G06F 19/3418
USPC .......................................... 714/4.21; 712/28
See application file for complete search history.

(56) References Cited

U.S. PATENT DOCUMENTS

| | | | | |
|---|---|---|---|---|
| 5,787,249 A | * | 7/1998 | Badovinatz ........... | G06F 9/5061 709/201 |
| 5,790,772 A | * | 8/1998 | Badovinatz ......... | G06F 11/1443 709/201 |
| 5,948,112 A | * | 9/1999 | Shimada ............. | G06F 11/1407 714/16 |
| 5,996,087 A | * | 11/1999 | Badovinatz ......... | G06F 11/1425 714/4.1 |
| 6,625,751 B1 | * | 9/2003 | Starovic .............. | G06F 11/1484 714/11 |
| 6,763,369 B1 | * | 7/2004 | Ytuarte ................ | H04Q 3/0091 379/269 |
| 7,689,873 B1 | | 3/2010 | Bennett et al. | |
| 2004/0205398 A1 | | 10/2004 | Osborn et al. | |
| 2005/0100156 A1 | * | 5/2005 | Ashdown ............ | H04M 7/0009 379/221.08 |

(Continued)

OTHER PUBLICATIONS

Rakitin, "Coping with defective software in medical devices", 2006, IEEE, p. 1-6.*

(Continued)

*Primary Examiner* — Bryce Bonzo
*Assistant Examiner* — Jeison C Arcos
(74) *Attorney, Agent, or Firm* — Kilpatrick Townsend & Stockton LLP (57) ABSTRACT

A system for applying a recovery mechanism to a network of medical diagnostics instruments is provided herein. The system includes the following: a plurality of medical diagnostics instruments, each associated with a network connected component; a plurality of communication modules, each associated with a corresponding one of the plurality of network connected components, wherein each one of the plurality of communication modules is arranged to report on malfunctioning components that are network connected with the corresponding component, and a recovery module, configured to: (i) obtain reports from the communication modules; (ii) re-establish the malfunctioning components; and (iii) notify all communication modules of the re-establishment of the malfunctioning components, wherein the communication modules are further configured to re-establish connection between the corresponding components and the re-established components.

18 Claims, 8 Drawing Sheets

(56) References Cited

U.S. PATENT DOCUMENTS

| | | |
|---|---|---|
| 2006/0075301 A1 | 4/2006 | Fossum et al. |
| 2006/0149837 A1 | 7/2006 | Weiner et al. |
| 2006/0253009 A1* | 11/2006 | Stubbs ............... A61N 1/362 600/323 |
| 2006/0253163 A1* | 11/2006 | Stubbs ............... A61N 1/3706 607/27 |
| 2007/0251835 A1* | 11/2007 | Mehta ............. A61B 5/14532 205/783 |
| 2007/0253021 A1* | 11/2007 | Mehta ............... A61B 5/0002 358/1.15 |
| 2007/0255250 A1* | 11/2007 | Moberg ............... A61M 5/142 604/503 |
| 2008/0172421 A1 | 7/2008 | Birnbaum et al. |
| 2010/0023798 A1 | 1/2010 | Meijer et al. |
| 2010/0037103 A1 | 2/2010 | Helmecke et al. |
| 2010/0292544 A1* | 11/2010 | Sherman ............... A61B 5/00 600/300 |
| 2011/0176490 A1 | 7/2011 | Mehta et al. |
| 2013/0247194 A1* | 9/2013 | Jha et al. ............ H04L 63/1425 726/23 |

OTHER PUBLICATIONS

International Search Report and Written Opinion of PCT/US12/65855 mailed on Feb. 5, 2013, 7 pages.

International Report on Patentability in related PCT/US2012/065855 mailed on Jun. 19, 2014, 8 pages.

CN201280066236.4, Office Action, Dec. 7, 2015.

EP12855663.6, Extended European Search Report, Jul. 31, 2015, 7 pages.

* cited by examiner

SUPERVISING AND RECOVERING SOFTWARE COMPONENTS ASSOCIATED WITH MEDICAL DIAGNOSTICS INSTRUMENTS

BACKGROUND

1. Technical Field

The present invention relates to the field of monitoring software components and more specifically, to the monitoring and recovering of software components associated with medical diagnostics instruments.

2. Discussion of Related Art

There is an ongoing trend of more and more diagnostics instruments becoming connected via a communication network for both monitoring and managing purposes. One of the characteristics of the data being processed is that it is usually private medical data. This requirement imposes, inter alia, data security measures. Additionally, as diagnostics instruments may be required around the clock, it would be advantageous to reduce mean time between failures of the diagnostics instrument.

BRIEF SUMMARY

One aspect of the invention provides a system for applying a recovery mechanism to a network of medical diagnostics instruments. The system may include the following features: a plurality of medical diagnostics instruments, each associated with a network connected component; a plurality of communication modules, each associated with a corresponding one of the plurality of network connected computer software components, wherein each one of the plurality of communication modules is arranged to report on malfunctioning computer software components that are network connected with the corresponding component, and a recovery module, configured to: (i) obtain reports from the communication modules; (ii) re-establish the malfunctioning computer software components; and (iii) notify all communication modules of the re-establishment of the malfunctioning computer software components, wherein each communication module is further configured to re-establish a connection between the one of the plurality of the computer software components and the re-established computer software components.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

For a better understanding of the invention, the usages of the following terms in the present disclosure are defined in a non-limiting manner:

The terms "component" and "software component," as used herein in this application, is defined as a software application comprised of business logic, a communication layer, a subscription manager and a service component.

The term "network," as used herein in this application, is defined as an infrastructure that enables an exchange of data between two or more nodes, such as the aforementioned components. In a non-limiting private case, the two or more nodes may reside on a single computer.

The term "communication module," as used herein in this application, is defined as the module that is associated with a component and responsible for: (i) reporting failure of other components that are network connected to the component; and (ii) re-establish connection between a re-established component and the corresponding component.

The term "recovery module," as used herein in this application, is defined as the module that is responsible for the activity status of components in the system.

The term "Configuration Manager Service (CMS)," as used herein in this application, is defined as the collection of procedures used to manage workflow in a collaborative environment. These procedures may be manual or computer-based.

The term "Window Communication Foundation (WCF)," as used herein in this application, is defined as an Application Programming Interface (API) in the .NET framework for building connected, service-oriented applications.

The term "WCF façade," as used herein in this application, is defined as a service that allows a WCF client to access the components that are being serviced.

The term "IsAlive poll," as used herein in this application, is defined as a message that is sent from a client of a component in CMS to the communication module of its corresponding component in order to check the activity status of the component.

The term "Watchdog Mechanism," as used herein in this application, is defined as the mechanism that is responsible for checking the activity status of components every specified period of time.

The term "business logic module," as used herein in this application, is defined as the module in a component that actually provides services to other components and requests services from other services.

The term "exception," as used herein in this application, is defined as the message thrown by a program when the normal flowchart conditions were not met.

The term "Method call," as used herein in this application, is defined as the request from a component to perform a task.

Figure 1A:
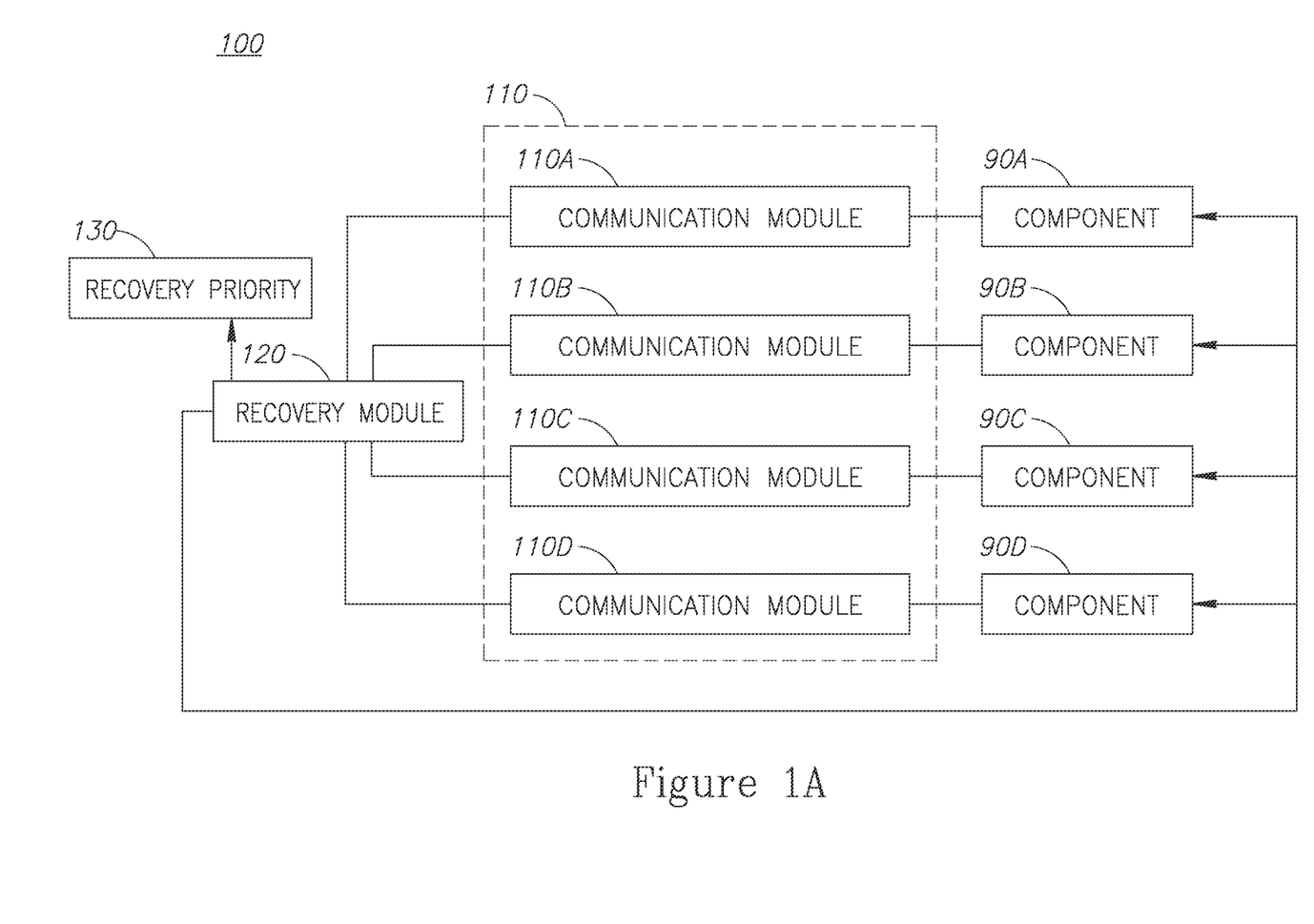
FIG. 1A is a high level schematic block diagram of a recovery mechanism in an environment of networked components according to some embodiments of the invention.

FIG. 1A is a high level schematic block diagram of a recovery mechanism 100 in an environment of networked components 90A-90D, according to some embodiments of the invention. Recovery mechanism 100 may include a plurality of communication modules 110A-110D, each associated with a corresponding one of networked components 90A-90D. Each communication module 110, for example, communication module 110A, is arranged to report on malfunctioning components, for example, components 90B and 90C that are networked with communication module 110A via corresponding component 90A. Additionally, recovery mechanism 100 may further include a recovery module 120 that is arranged to: (i) obtain reports from the communication modules 110A-110D; (ii) re-establish malfunctioning components for example, components 90B and 90C; and (iii) notify all communication modules 110A-110D of the re-establishment of the malfunctioning components (e.g., components 90B and 90C).

In response to the re-establishing carried out by recovery mechanism 100 operation, and continuing with the example above, a notification to the communication modules 110A-110D may be sent and communication modules 110A-110D in turn may re-establish connections between their corresponding components 90A and 90D and the re-established components 90B and 90C. Additionally, the re-establishing of the malfunctioning components 90B and 90C by the recovery module 120 may be carried out according to a specified priority list 130 of components being recovery priority.

Figure 1B:
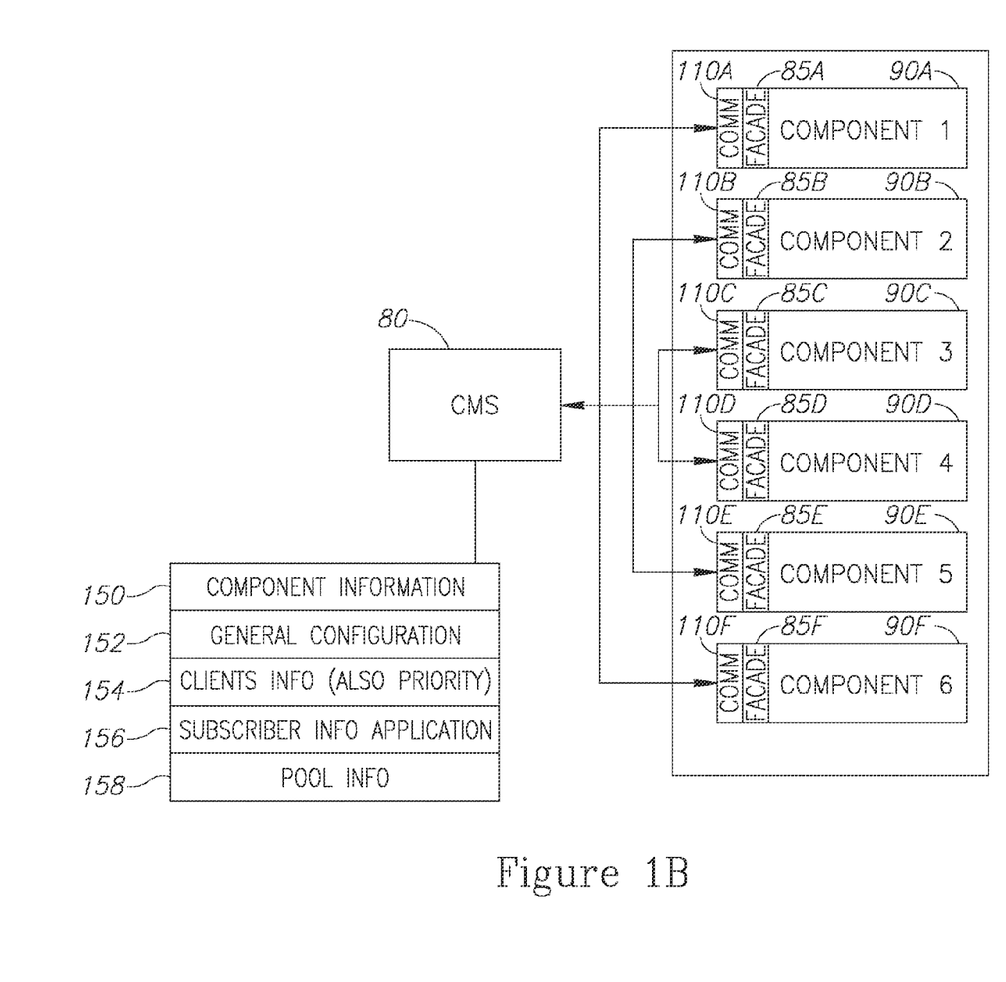
FIG. 1B is a high level schematic and detailed block diagram of the recovery mechanism in an environment of networked components, according to some embodiments of the invention.

FIG. 1B illustrates a more detailed expression of recovery mechanism implemented, in a non-limiting example within a context of a Configuration Manager Service (CMS) 80, which manages the following: (i) information of the component 150; (ii) general configuration 152; (iii) info of clients and priority 154; (iv) application of subscriber information 156; and (v) pool information 158. The connection between communication modules 110A-110F and its corresponding component 90A-90F may be implemented via WCF façades 85A-85F that may provide a simplified interface to components 90A-90F. The aforementioned recovery process may be triggered to operate by (i) the CMS 80; (ii) any component 90A-90F; and/or (iii) communication module 110E-110F.

Table 1 illustrates a non-limiting example for priorities and associated sets of components 90A-90F to be recovered are provided herein.

| Malfunctioning Component | Priority list | Recover Components |
|---|---|---|
| 90A | Critical | All |
| 90B | Medium | 90B, 90C |
| 90C | Medium | 90C, 90B |
| 90D | Low | 90D |
| 90E | Low | 90E |
| 90F | High | 90F, 90B, 90C |

Consistent with some embodiments of the present invention the recovery may be carried out by re-establishing malfunctioning components 90A-90F group-wise, according to specified inter-dependencies among networked components 90A-90F, to quickly recover functionality associated with the groups of components 90A-90F.

Figure 2A:
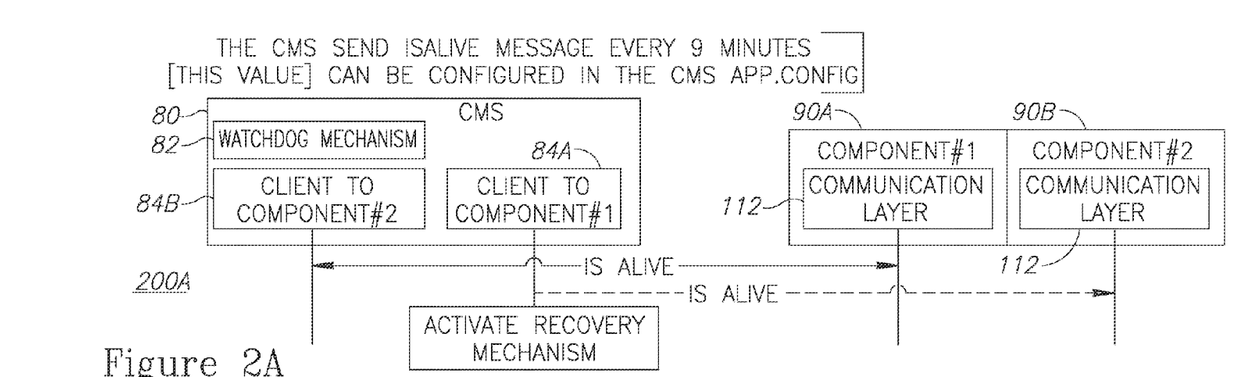
FIGS. 2A and 2B are sequence diagrams illustrating aspects according to some embodiments of the invention.

FIG. 2A illustrates an IsAlive poll 200A carried out by CMS 80. CMS 80 keeps a client 84 for every component in the system (84A, 84B, and so forth), either locally or remotely. Watchdog mechanism 82 may check the operation of the components (not shown here) every specified period of time. For example, CMS 80 may send an IsAlive poll every x minutes, with x configurable via a configuration. Client 84A in CMS 80 may receive an exception from the service that indicated malfunctioning component.

Figure 2B:
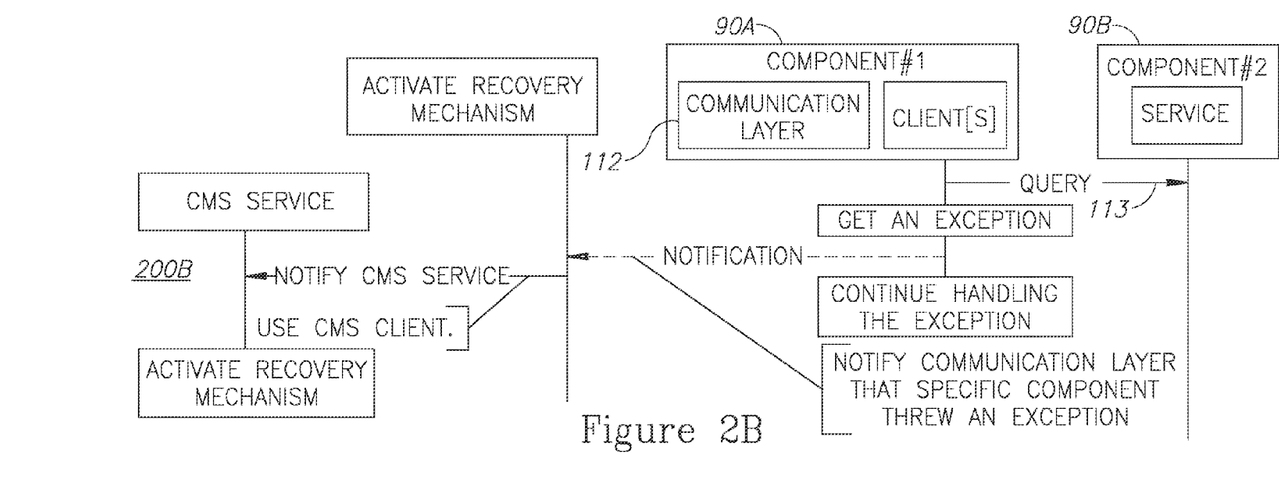

FIG. 2B illustrates the activation 200B of recovery module by one of communication modules 110A, according to one embodiment. Any component 90, for example component 90B, may throw an exception to component 90A, as a response to a query 113, namely a request for service from the component 90B. Consequently, communication module 110A may identify that the associated component 90A received an exception which was thrown by component 90B, and notifies business logic module 114 its communication layer 112 namely, communication module 110A, that it received an exception, as an indication of a malfunctioning component 90B.

Then, communication layer 112 may use its corresponding CMS client 84 to notify CMS 80 that the specific service provider, namely the malfunctioning component 90B, threw an exception. Then, CMS 80 may start recovery mechanism 100.

As a result, recovery module 120 may attempt to reload malfunctioning component 90B that has crashed. In case recovery module 120 failed to reload crashed component 90B and component 90B was specified as critical in priority list 130, recovery module 120 activates a termination operation to component 90B.

Further, recovery mechanism 100 may facilitate priority based recovery mechanism, using a priority list 130 of components. Recovery mechanism 100 may support distribution of: (i) local components that are running on the same computer; and (ii) distributed components that are running on a network.

Figure 3A:
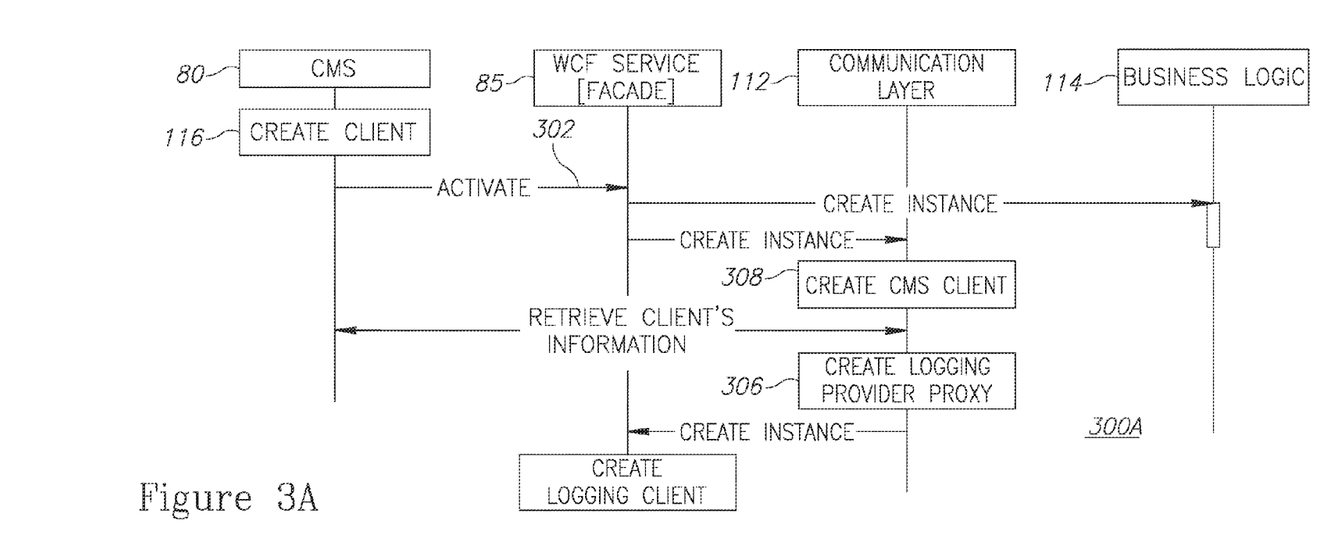
FIGS. 3A and 3B are sequence diagrams illustrating other aspects according to some embodiments of the invention.

FIG. 3A is a sequence diagram illustrating an activation sequence 300A of WCF environment by CMS 80, according to some embodiments of the invention. CMS 80 creates a client 116 that activates 302 WCF façade 85. Then WCF façade 85 creates an instance of a business logic module 114 and an instance of a communication module 110. Consequently, communication module (not shown here) creates a client 116 to communicate with CMS client (not shown here) to exchange information. Then, communication module 110 may perform logging provider proxy 306 and creates an instance of logging client in WCF façade service 85.

Figure 3B:
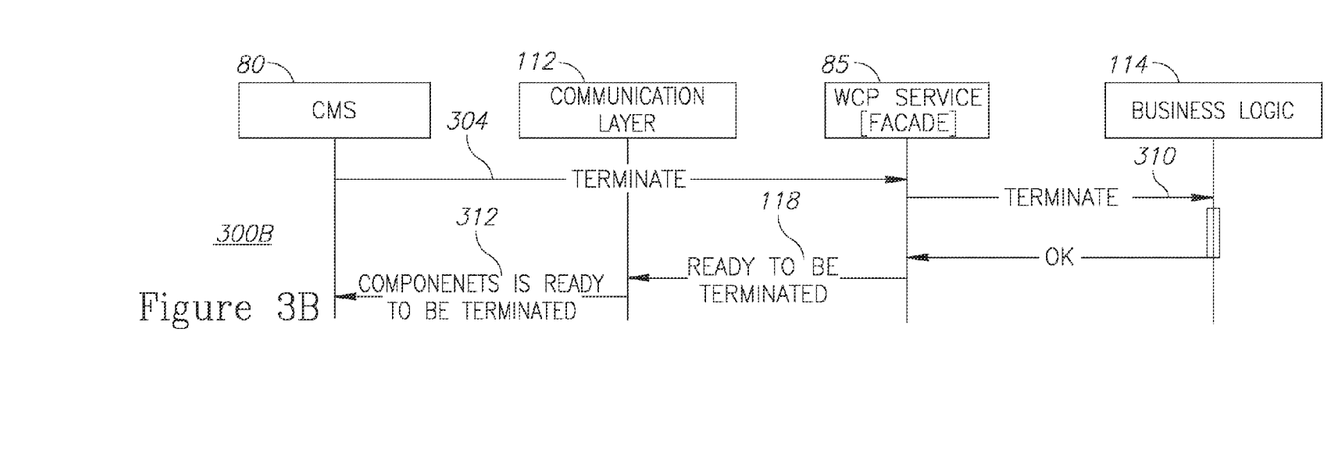

FIG. 3B is a sequence diagram illustrating a termination sequence 300B of WCF environment by CMS 80, according to some embodiments of the invention. Termination operation 304 starts with CMS 80 sending a termination message 310 to communication layer 112. In response communication module (not shown here) in communication layer 112 sends termination message 310 to business logic module 114. Business logic module 114 sends response to WCF façade service 85 when it is ready to terminate via its communication layer 112. Then WCF façade service 85 sends ready-to-be-terminated message 118 to communication module 110. In response, communication module 110 sends component-is-ready-to-be-terminated message 312 to CMS 80.

Figure 4:
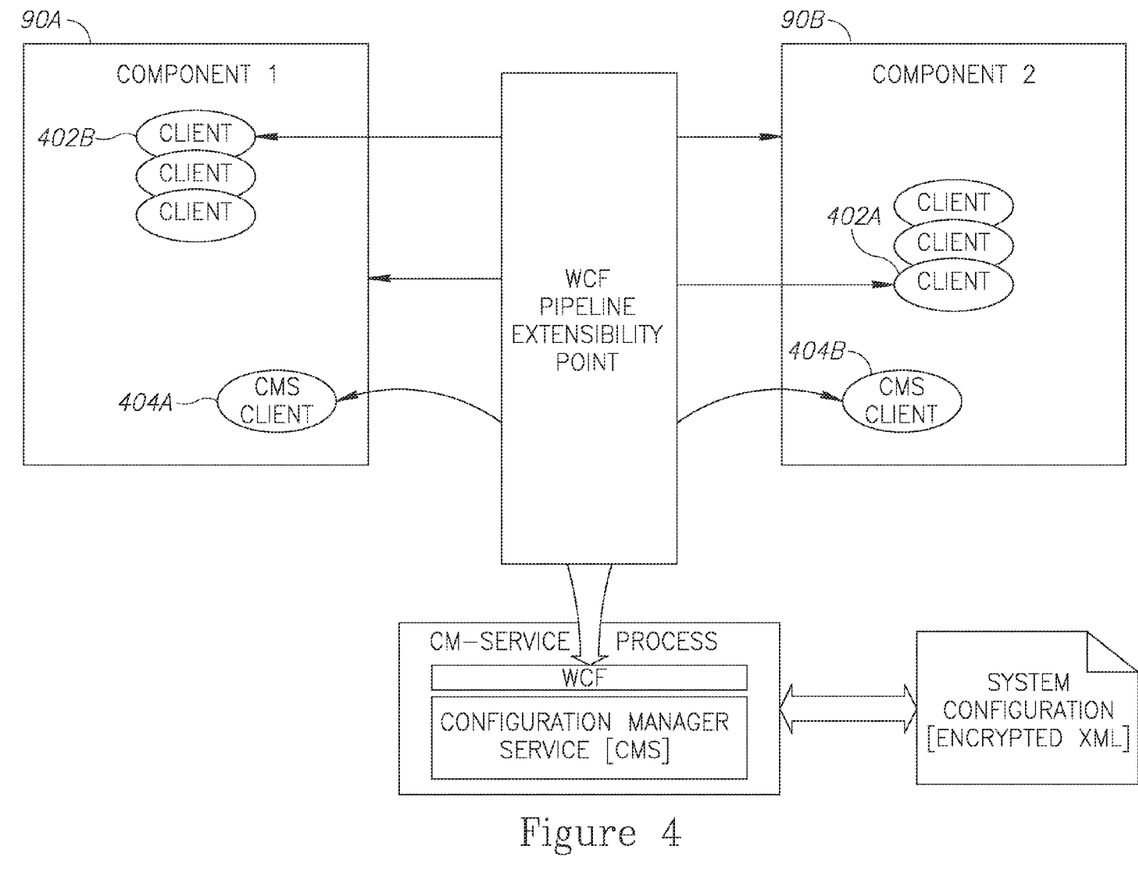
FIG. 4 is a block diagram illustrating establishing a connection between each other, to some embodiments of the invention.

FIG. 4 is a block diagram illustrating two components establishing a connection between each other, to some embodiments of the invention. Each component may consist of several clients to provide services to other components. For example, a component 90A may provide services to another component 90B via a client 402B and component 90B may provide services to component 90A via a client 402A. Further, each component may include a client to CMS (not shown here), for example, CMS client 404A in component 90A and CMS client 404B in component 90B. Component 90A may retrieve configuration information via client 404A and component 90B may retrieve configuration information via CMS client 404B. An example of the configuration information that may be retrieved is endpoint of service of other components.

Figure 5:
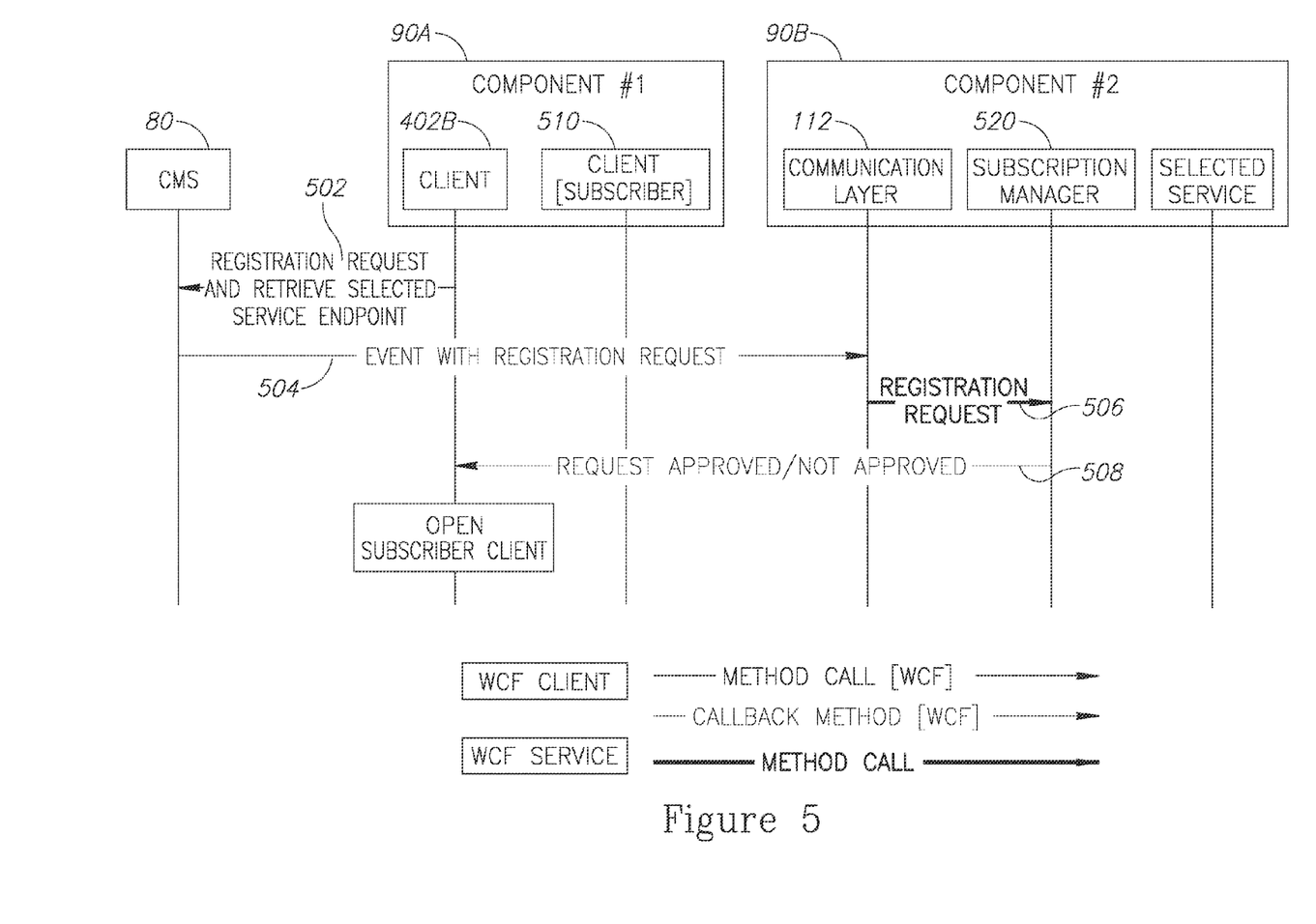
FIG. 5 is sequence diagram illustrating communication between various layers in two components that are supervised by CMS, to some embodiments of the invention.

FIG. 5 is a sequence diagram illustrating a subscription process between two components 90A and 90B that are supervised by CMS 80. The subscription process is performed via various layers, according to some embodiments of the invention. The subscription process may start when component 90A requires a service from component 90B. Component 90A may send a registration request 502 message to CMS 80 and may retrieve endpoints of the subscription manager that refers to the service required using a client for CMS 80. Then, CMS 80 creates an event with registration request 504 to communication module (not shown here) of component 90B in communication layer 112. The registration request 504 refers to the selected service. The type of request message sent is a callback method. Then, in component 90B communication module (not shown here) may reopen the subscription manager module 520 and may send a registration request 506 to the subscription manager module 520. The type of request message sent is a Method call. In response, subscription manager module 520 may send a notification of approval or denial 508 to client 402B in component 90A. The notification may include an endpoint of the selected service. The type of message sent is a callback method. In case subscription manager sent an approval message to component 90A, component 90A opens subscriber client 510. The type of request message sent is a callback method.

Figure 6:
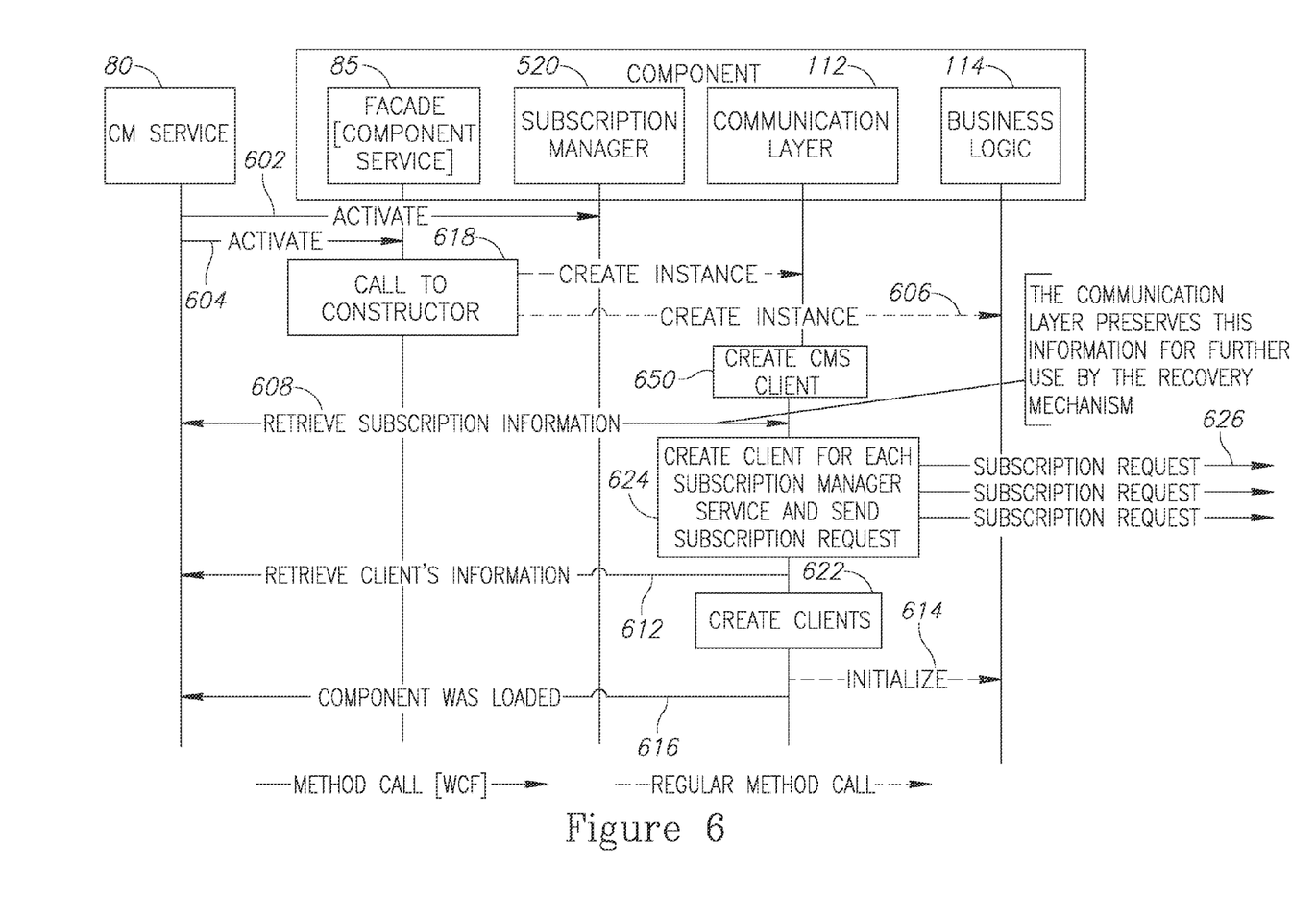
FIG. 6 is a sequence diagram illustrating startup of modules in a component, when a component receives a request for service, to some embodiments of the invention.

FIG. 6 is a sequence diagram illustrating startup of modules in a component, when a component receives a request for service, to some embodiments of the invention. CMS 80 may send a method call to activate subscription manager module 520. CMS 80 sends a method call to activate WCF façade service 85. In response, WCF façade service 85 may call for service default constructor 618. The service default constructor 618 may create an instance of business logic module 114 by sending a regular method call. Further WCF façade service 85 may create an instance in communication layer 112 and pass the business logic instance 114 as an argument for future usage.

Then, the communication layer 112 may create a client 650 to communicate with the CMS 80. The communication layer 112 may use this client 650 to retrieve information from the CMS 80. The information that may be retrieved is: (i) subscription information with endpoints of all subscription manager services that the component may need to register to; (ii) client information with endpoints of all services that the component may be authorized to attach to. Based on the information retrieved 608 from the subscription manager module 520 taken from the CMS 80, the communication layer 112 may create a client 624 and may send subscription requests 626. Further, the communication layer 112 may create a regular client 622 for all services based on information about the clients taken from the CMS 80. Then, the communication layer 112 may call to initialize a method in the WCF façade 85 for additional initializations. Then, the communication layer (not shown here) may notify the CMS 80 that the component was loaded.

Figure 7:
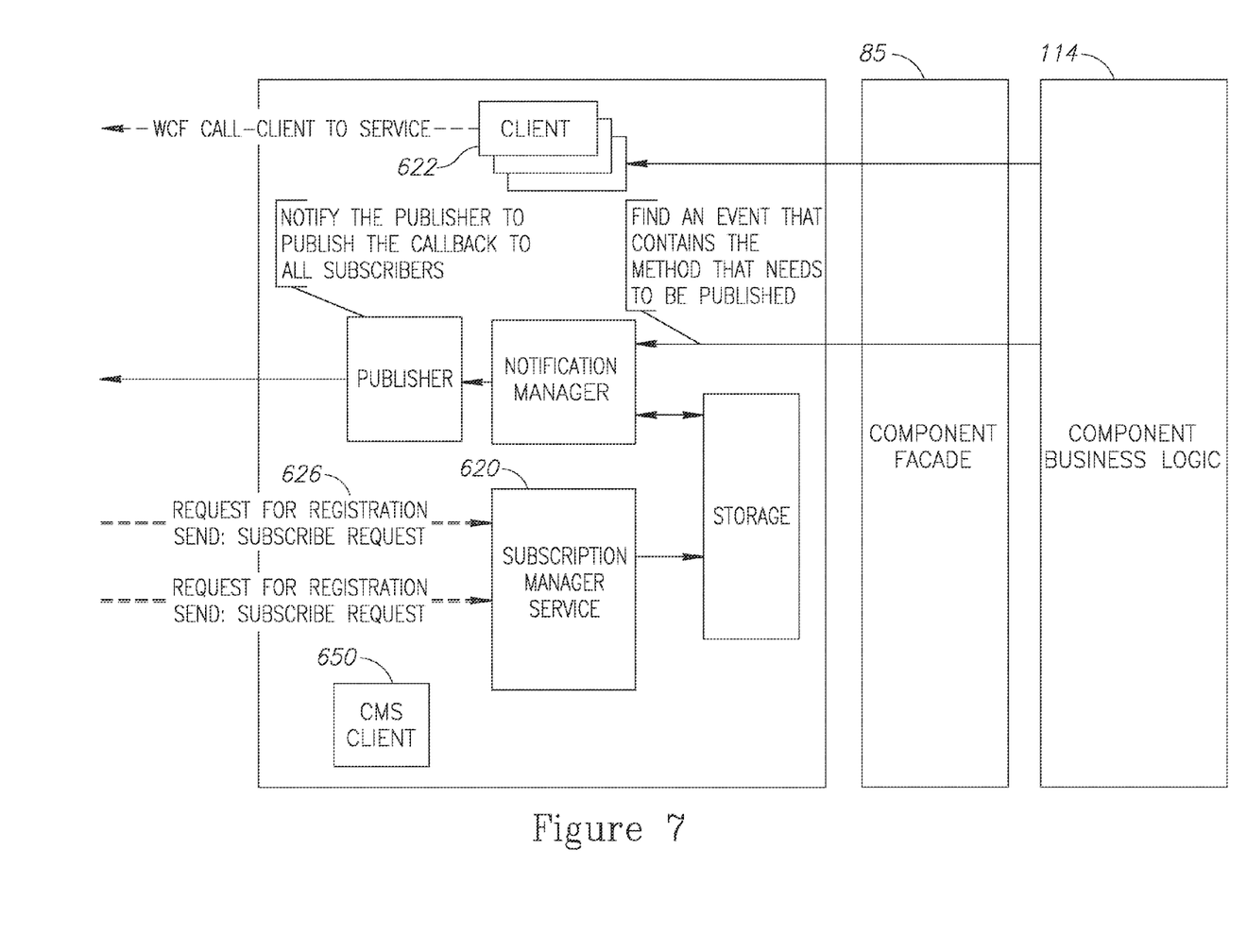
FIG. 7 is a block diagram illustrating communication class library, to some embodiments of the invention.

FIG. 7 is a block diagram illustrating a communication class library, according to some embodiments of the invention. The communication class library allows each component to communicate with the CMS (not shown here) to: (1) retrieve information about a client that the component wishes to open; (2) get notification(s) in case another process crashed; and (3) get notification(s) of a component reload and recreate a client for reloaded component and register to its events. The communication class library allows each component to register the component to other process events and open clients upon other process services.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above. In particular, the invention is not limited to those diagrams or to the corresponding descriptions. For example, flow need not move through each illustrated box or state, or in exactly the same order as illustrated and described. Methodologies described herein may be implemented by various means depending upon applications according to particular features or examples. For example, such methodologies may be implemented in hardware, firmware, software, discrete/fixed logic circuitry, any combination thereof, and so forth. In a hardware or logic circuitry implementation, for example, a processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other devices or units designed to perform the functions described herein, or combinations thereof, just to name a few examples.

For a firmware or software implementation, the methodologies may be implemented with modules (e.g., procedures, functions, etc.) having instructions that perform the functions described herein. Any non-transitory computer- and/or machine-readable medium embodying instructions may be used in implementing the methodologies described herein. For example, software codes from a computer program product or other source may be stored in a memory and executed by a processor. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored. In at least some implementations, one or more portions of the herein described storage media may store signals representative of data or information as expressed by a particular state of the storage media. For example, an electronic signal representative of data or information may be "stored" in a portion of the storage media (e.g., memory) by affecting or changing the state of such portions of the storage media to represent data or information as binary information (e.g., ones and zeros). As such, in a particular implementation, such a change of state of the portion of the storage media to store a signal representative of data or information constitutes a transformation of storage media to a different state or thing.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A system for applying a recovery mechanism to a plurality of computer software components that control medical diagnostics, the system comprising:
   a plurality of medical diagnostics instruments, each associated with a computer software component;
   a plurality of communication modules, each associated with a corresponding one of the plurality of the computer software components, wherein each one of the plurality of communication modules is arranged to report on malfunctioning computer software components; and
   a recovery module, configured to:
   (i) periodically obtain reports from the communication modules every certain period of time, the reports enabling a determination of whether computer software components are malfunctioning;
   (ii) reload the malfunctioning computer software components, wherein reloading the malfunctioning computer software component of a first medical diagnostics instrument comprises creating, at a communication layer, a client for providing a service to another computer software component of a second medical diagnostic instrument; and
   (iii) notify all communication modules of the reloading of the malfunctioning computer software components;
   wherein each communication module is further configured to re-establish a connection between the corresponding one of the plurality of the computer software components and the reloaded computer software components.

2. The system according to claim 1, wherein the recovery module is further configured to reload the malfunctioning computer software components according to a specified priority list of computer software components.

3. The system according to claim 1, wherein the recovery module is further configured to reload critical malfunctioning computer software components prior to other malfunctioning computer software components according to specified criteria.

4. The system according to claim 1, wherein the recovery module is further configured to reload the malfunctioning computer software components groupwise, according to specified inter-dependencies among network-connected components.

5. The system according to claim 1, wherein the recovery module is further configured to terminate an operation of one or more network-connected computer software components upon failure of a reloading thereof.

6. The system according to claim 1, wherein the recovery module is further configured to carry out the notifying based on a predefined priority order of computer software components.

7. A method of applying a recovery mechanism to software components that control medical diagnostics instruments, the method comprising:
   monitoring a plurality of medical diagnostics instruments, each associated with a software component via a plurality of communication modules;
   every certain period of time, obtaining a report from the communication module, each report enabling a determination of whether software components are malfunctioning;
   determining, from an obtained report, an occurrence of a malfunctioning of a software component;
   reloading the malfunctioning software component upon analyzing the obtained report, wherein reloading the malfunctioning software component of a first medical diagnostics instrument comprises creating, at a communication layer, a client for providing a service to another software component of a second medical diagnostic instrument;
   notifying all communication modules of the reloading of the malfunctioning software component; and
   re-establishing a connection between the software components and the re-established software component, via the communication modules.

8. The method according to claim 7, wherein the reloading of the malfunctioning software component is carried out according to a specified priority list of software components.

9. The method according to claim 7, wherein reloading of the malfunctioning software component is carried out such that it is reloaded prior to other malfunctioning software components, according to specified criteria.

10. The method according to claim 7, wherein the reloading of the malfunctioning software component is carried out according to specified inter-dependencies among network-connected software components.

11. The method according to claim 7, further comprising terminating an operation of one or more network-connected software components upon failure of a reloading thereof.

12. The method according to claim 7, wherein the notifying is carried out based on a predefined priority order of software components.

13. A computer program product embodied on a non-transitory computer-readable medium, the computer program product comprising:
   computer code for monitoring software components associated with a medical instrument, each associated with a software component via a plurality of communication modules;
   computer code for obtaining, every certain period of time, a report from the communication modules, each report enabling a determination of whether software components are malfunctioning;
   computer code for determining, from an obtained report, an occurrence of a malfunctioning of a software component;

computer code for reloading the malfunctioning software component upon analyzing the obtained report, wherein reloading the malfunctioning software component of a first medical diagnostics instrument comprises creating, at a communication layer, a client for providing a service to another software component of a second medical diagnostic instrument;

computer code for notifying all communication modules of the reloading of the malfunctioning software component; and computer code for re-establishing a connection between the software components and the reloaded software component, via the communication modules.

14. The computer program product according to claim 13, wherein the reloading of the malfunctioning software component is carried out according to a specified priority list of components.

15. The computer program product according to claim 13, wherein the reloading of the malfunctioning software component is carried out such that it is reloaded prior to other malfunctioning software components, according to specified criteria.

16. The computer program product according to claim 13, wherein the reloading of the malfunctioning software component is carried out group-wise, according to specified inter-dependencies among network-connected software components.

17. The computer program product according to claim 13, further comprising computer code for terminating an operation of one or more network-connected software components upon failure of a reloading thereof.

18. The computer program product according to claim 13, wherein the notifying is carried out based on a predefined priority order of software components.

* * * * *